(12) United States Patent
Borgschulte et al.

(10) Patent No.: US 9,027,548 B2
(45) Date of Patent: May 12, 2015

(54) AEROSOL GENERATING DEVICE AND INHALATION THERAPY UNIT PROVIDED WITH THIS DEVICE

(75) Inventors: Markus Borgschulte, Munich (DE); Wolfgang Achtzehner, Alling (DE); Andreas Pfichner, Unterhaching (DE); Norbert Kamm, Birkenfeld (DE)

(73) Assignee: PARI Pharma GmbH, Starnberg (DE)

( * ) Notice: Subject to any disclaimer, the term of this patent is extended or adjusted under 35 U.S.C. 154(b) by 1453 days.

(21) Appl. No.: 11/884,196

(22) PCT Filed: Jan. 17, 2006

(86) PCT No.: PCT/EP2006/000363
§ 371 (c)(1),
(2), (4) Date: Jun. 11, 2008

(87) PCT Pub. No.: WO2006/084546
PCT Pub. Date: Aug. 17, 2006

(65) Prior Publication Data
US 2008/0308096 A1     Dec. 18, 2008

(30) Foreign Application Priority Data

Feb. 11, 2005   (DE) .......................... 10 2005 006 374

(51) Int. Cl.
*B05B 17/06* (2006.01)
*B05B 17/00* (2006.01)
(Continued)

(52) U.S. Cl.
CPC .......... *B05B 17/0646* (2013.01); *A61M 11/005* (2013.01); *A61M 15/0085* (2013.01)

(58) Field of Classification Search
CPC ............ A61M 11/005; A61M 15/0085; B05B 17/0646

USPC ............ 128/200.14, 200.16, 200.23, 203.12, 128/203.14, 203.16, 203.26–203.27; 700/283; 239/102, 102.1; 346/75, 140; 347/47; 310/326, 327

See application file for complete search history.

(56) References Cited

U.S. PATENT DOCUMENTS 3,812,854 A  * 5/1974  Michaels et al. ......... 128/200.16
4,605,167 A    8/1986  Maehara et al.
(Continued)

FOREIGN PATENT DOCUMENTS

DE         23 42 470 A1    3/1974
DE     10 2005 006374 B3   7/2006
(Continued)

OTHER PUBLICATIONS

Office Action mailed Jan. 9, 2006 from corresponding German Patent No. DE 10 2005 006 374.

(Continued)

*Primary Examiner* — Tan-Uyen (Jackie) T Ho
*Assistant Examiner* — Mark K Han
(74) *Attorney, Agent, or Firm* — Wolf, Greenfield & Sacks, P.C.

(57) ABSTRACT

An aerosol generating device includes a membrane for atomizing a liquid; an actuating device, which is coupled to the membrane so that this membrane is set in oscillatory motion when activated by electric signals; and a flexible substrate, which has electric lines for supplying electric signals to the actuating device and is designed for fastening the aerosol generating device to a fastening area of an inhalation therapy unit, and on which the membrane and the actuating device are held.

22 Claims, 6 Drawing Sheets

(51) Int. Cl.
*A61M 11/00* (2006.01)
*A61M 15/00* (2006.01)

(56) References Cited

U.S. PATENT DOCUMENTS

| | | | |
|---|---|---|---|
| 4,702,418 A | 10/1987 | Carter et al. | |
| 5,551,416 A * | 9/1996 | Stimpson et al. | 128/200.16 |
| 6,382,522 B2 * | 5/2002 | Tomkins et al. | 239/102.2 |
| 6,539,937 B1 * | 4/2003 | Haveri | 128/200.21 |
| 6,769,626 B1 * | 8/2004 | Haveri | 239/102.2 |
| 6,978,779 B2 * | 12/2005 | Haveri | 128/200.16 |
| 7,360,536 B2 * | 4/2008 | Patel et al. | 128/200.14 |
| 7,458,372 B2 | 12/2008 | Feiner et al. | |
| 7,771,642 B2 * | 8/2010 | Power et al. | 264/272.16 |
| 7,775,459 B2 * | 8/2010 | Martens et al. | 239/102.2 |
| 7,883,031 B2 * | 2/2011 | Collins et al. | 239/338 |
| 8,511,581 B2 * | 8/2013 | Urich et al. | 239/102.1 |
| 2003/0196660 A1 * | 10/2003 | Haveri | 128/203.12 |
| 2003/0218077 A1 * | 11/2003 | Boticki et al. | 239/102.1 |
| 2004/0188534 A1 | 9/2004 | Litherland et al. | |
| 2005/0034719 A1 * | 2/2005 | Feiner et al. | 128/200.21 |

FOREIGN PATENT DOCUMENTS

| | | |
|---|---|---|
| EP | 1219314 A1 | 7/2002 |
| WO | WO 00/53337 A1 | 9/2000 |
| WO | WO 02/087774 A1 | 11/2002 |
| WO | WO 03/068412 A1 | 8/2003 |
| WO | WO 2004/014569 A1 | 2/2004 |
| WO | WO 2004/039442 A1 | 5/2004 |

OTHER PUBLICATIONS

Preliminary Report on Patentability mailed Aug. 23, 2007 from corresponding International Application No. PCT/EP2006/000363.

* cited by examiner ced manner for a function which is required in any event, namely the mounting of the aerosol generator, without negatively affecting the oscillatory behaviour of the oscillatable structure.

AEROSOL GENERATING DEVICE AND INHALATION THERAPY UNIT PROVIDED WITH THIS DEVICE

The present invention relates to an aerosol generating device and an inhalation therapy unit in which the aerosol generating device is provided.

A drug-containing liquid in the form of a respirable aerosol, which is generated by an appropriate aerosol generator in the inhalation therapy unit, is made available to a patient for inhalation in an inhalation therapy unit.

In membrane aerosol generators, a therapeutically high-quality aerosol of the smallest drops of liquid is generated with the help of a membrane which is set in oscillatory motion by an actuating device, for example a piezoelectric ring. In order to enable a satisfactory oscillation of the membrane and the actuating device, it is necessary to fasten the oscillating structure in the inhalation therapy unit such that the oscillations do not have a negative effect on the oscillatable structure.

This requirement has led in the prior art to the proposal of a fastening for the oscillating structure such that the oscillation of the membrane and the actuating device experiences as little damping as possible. For this purpose, in the prior art, the aerosol generator, as disclosed for example in US 2004/0188534, is fastened on radial ligaments such that the ligaments decouple the aerosol generator's oscillation from the aerosol generator's fastening and thus the aerosol generator experiences as little damping as possible on actuation. For this purpose, US 2004/0188534 proposes ligaments projecting radially from the aerosol generator. In order to enable space-saving fastening, these ligaments are bent backwards or forwards once or a plurality of times out of the plane of the aerosol generator. This design only achieves the desired aim with limited success and is too complicated in practice as the proposal is geared entirely to the fastening.

Furthermore, an oscillating suspension of an aerosol generator is known from WO 2004/014569 in which ligament-shaped suspensions are likewise provided which do not, however, extend exclusively radially but which have a tangential component and at the same time remain in the plane of the aerosol generator. Thus a space-saving oscillatable arrangement is created which makes it possible to suspend the aerosol generator so that it is actually capable of oscillation. This proposal, however, is also restricted to the aerosol generator's suspension.

Thus the object of the present invention is to provide an aerosol generating device in which a suspension favourable to oscillation is implemented but which also at the same time covers further aspects of the aerosol generator's structural design.

This object is achieved by an aerosol generating device with the features according to claim 1.

Advantageous developments emerge from the subclaims.

Figure 1:
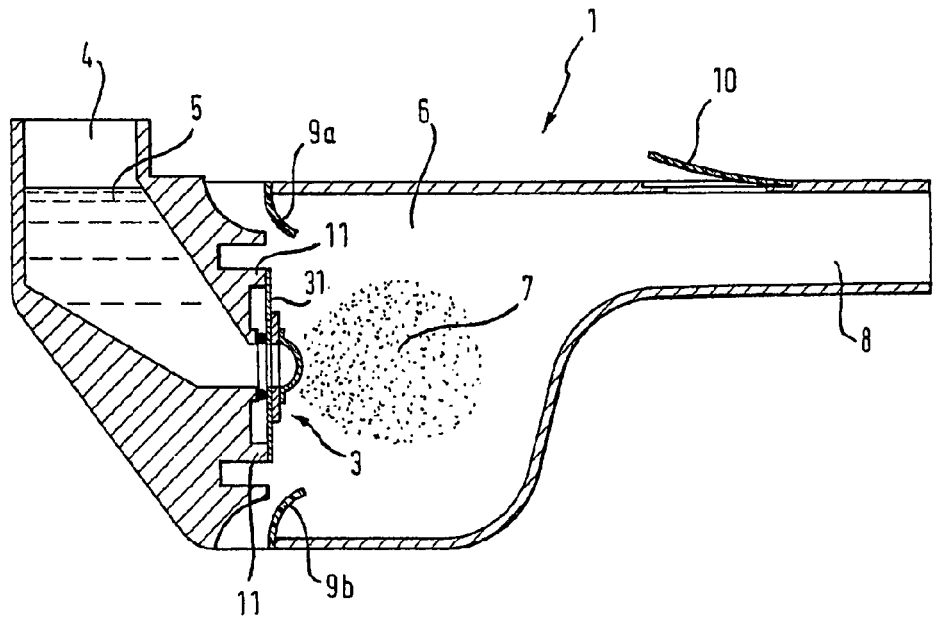
FIG. 1 shows a schematic representation of an inhalation therapy unit with an aerosol generating device according to the invention.

The construction of an exemplary inhalation therapy unit, which is fitted with an aerosol generating device according to the invention, is explained by way of introduction on the basis of FIG. 1 to clarify the area of use of an aerosol generating device described later in greater detail.

Inhalation therapy unit 1 shown by way of example comprises, in addition to an aerosol generating device 3 according to the invention, a reservoir 4 for a drug-containing liquid 5, which is supplied to aerosol generating device 3, and a nebulizing chamber 6, into which aerosol generating device 3 delivers aerosol 7 generated from the liquid, when aerosol generating device 3 is set in oscillatory motion. A patient inhales aerosol 7 by way of a mouthpiece 8, whereby additional inhaled air flows into nebulizing chamber 6 through inhalation valves 9a and 9b. If the patient exhales into nebulizing chamber 6, inhalation valves 9a and 9b close and the exhaled air escapes through an exhalation valve 10 which is located, for example, in mouthpiece 8 of inhalation therapy unit 1.

Figure 2A:
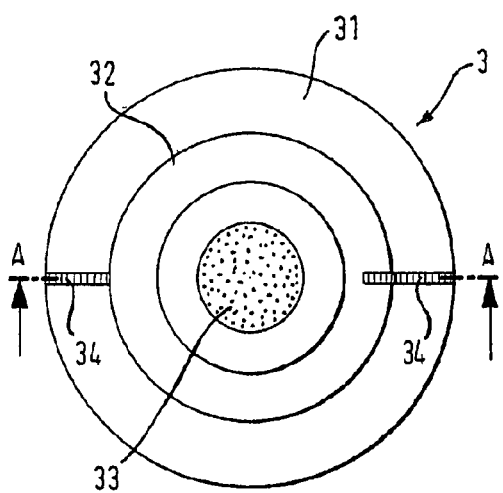
FIGS. 2a and 2b show an embodiment of an aerosol generating device according to the invention in a view from above and in a sectional view.
Figure 2B:
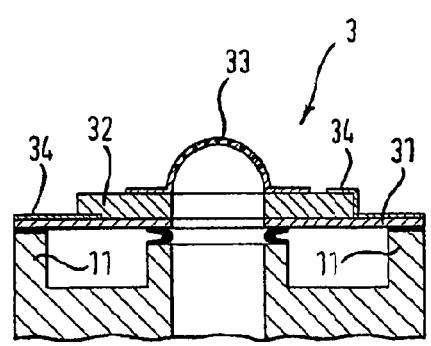

As FIG. 1 shows, aerosol generating device 3 is disposed in inhalation therapy unit 1 and is fastened for this purpose according to the invention to a fastening area 11 of inhalation therapy unit 1, for which purpose aerosol generating device 3 according to the invention has substrate 31 which will be explained in greater detail in the following with reference to FIG. 2. It should be noted at the same time that FIG. 2a shows a view from above onto an embodiment having a rotationally symmetrical design of an aerosol generating device according to the invention and FIG. 2b shows a sectional view along line A-A in FIG. 2a.

In the embodiment of the invention shown in FIG. 2, aerosol generating device 3 comprises a flexible substrate 31, an actuating device 32, which can be activated by means of electrical signals, and a membrane 33 which can be set in oscillatory motion by the actuating device in addition to electrical conductors 34 for supplying the actuating device with electrical signals. According to the invention, flexible substrate 31 is designed firstly for fastening of aerosol generating device 3 to a fastening area of an inhalation therapy unit, secondly for holding actuating device 32 and membrane 33 and thirdly for carrying electrical conductors 34. According to the invention, flexible substrate 31 thus serves, alongside its function as a carrier for electrical conductors, the additional purpose, on one hand, of fastening the aerosol generating device according to the invention in an inhalation therapy unit, and on the other, the purpose of holding actuating device 32 and membrane 33, which together form a structure which is to be set in oscillatory motion for aerosol generation, in a manner favourable to oscillation. Due to the flexibility of substrate 31, the oscillations performed by the oscillatable structure are not impaired or only impaired to a negligible extent but secure positioning of the oscillatable structure is achieved at the same time. Thus the invention utilises the flexibility of the conductive structure in an advantageous manner by using it for positioning the aerosol generator in a therapy unit and for decoupling the oscillation of the oscillating structure.

Particularly suitable as flexible substrate 31 are flexible printed circuit boards or flexible conductor boards/foils, for example of polyimide (PI), polyethylene naphthalate (PEN), polyester (PET) or another appropriate insulating material, for example with typical thicknesses ranging between 10 and 250 μm, onto which conductors made from Cu. Ag, Al or another conductive material, for example, are applied or in which such conductors are integrated. The construction of these circuit boards or conductor boards or foils may be single-layer or multiple-layer and may have a top layer.

As may be seen in FIG. 2*b*, flexible substrate 31 is designed for fastening of the aerosol generating device in an inhalation therapy unit by, for example, adapting the dimensions of flexible substrate 31 to the geometry of fastening area 11 and fixing is possible, for example by bonding, as shown in FIG. 2*b*, or by clamping, snapping in, inserting or in some other way.

Advantageously, a component of piezoelectric or some other material, which reacts to the electrical signals supplied and then ensures that membrane 33 is set in oscillatory motion, is suitable as actuating device 32.

Membrane 33 consists preferably of a metal and has a plurality of holes in a region formed for aerosol generation. Membrane 33 is preferably domed in the region significant for aerosol generation, as is shown for example in FIG. 2*b*.

In the embodiment of an aerosol generating device according to the invention shown in FIG. 2, actuating device 32 is disposed between flexible substrate 31 and membrane 33. FIG. 3 shows embodiments of aerosol generating devices according to the invention which are modified in respect of this arrangement. Thus, FIG. 3*a* shows an embodiment in which membrane 33 is disposed between flexible substrate 31 and actuating device 32, whilst FIGS. 3*b* and 3*c* show embodiments in which flexible substrate 31 is disposed between actuating device 32 and membrane 33. The only part of the inhalation therapy unit shown in the diagram in FIG. 3 is fastening area 11, which is necessary for describing the invention, whilst other details have been left out to simplify the diagram. Moreover, it should be noted in respect of FIG. 3*c* that here the basic conductor wiring through flexible substrate 31, which can be used in all embodiments, is also shown. The type of execution is known in conjunction with the flexible circuit boards and conductor boards/foils referred to above and may also be used in the most varied configuration with a flexible substrate according to the invention.

In all of the embodiments described so far, the oscillations required for aerosol generation are brought about by actuating device 32 in reciprocal action with membrane 33 and/or flexible substrate 31. For this purpose, actuating device 32 is connected, for example bonded or soldered, to membrane 33 and/or flexible substrate 31. The design of the structural details of flexible substrate 31, actuating device 32 and membrane 33 in addition to the joints make it possible to a great extent to influence the oscillation characteristics of the oscillatable structure and to define them within broad ranges. Electrical conductors 34 can also be included in the process.

Nevertheless, the design possibilities are restricted to the extent that flexible substrate 31 is designed according to the invention for fixing of the aerosol generator in a manner favourable for oscillation and thus as a rule is very thin just like membrane 33 which is also not very thick in practice due to the manufacture of the precisely defined holes. In particular to ensure the occurrence of flexural oscillations, according to a further embodiment of an aerosol generating device according to the invention as shown in FIG. 4, in addition to flexible substrate 31, actuating device 32 and membrane 33 as well as electrical conductors 34, a further substrate 35 is provided, which is preferably made of a metal and is tuned to actuating device 32 and joined thereto such that, on activation of actuating device 32 by means of applied electrical signals, flexural oscillations are set in motion, i.e. oscillations out of a plane which is spanned by flexible substrate 31, actuating device 32, membrane 33 or further substrate 35.

The sequence of the configuration of flexible substrate 31, actuating device 32, membrane 33 and further substrate 35 is just as modifiable in the embodiment shown in FIG. 4 as was explained in conjunction with the embodiments shown in FIG. 3 with the result that a description of the different possibilities is superfluous with reference to the explanations further up.

FIG. 5 shows various possibilities of fastening the flexible substrate to the fastening area of an inhalation therapy unit. FIG. 5*a* shows again the bonded joint between flexible substrate 31 and fastening area 11 referred to above. In this case, surface 101 of fastening area 11 forms the contact area for the bond either completely or at least in part. FIG. 5*b* shows a development in which a groove 102 is provided on fastening area 11, into which groove an edge, preferably the circumferential edge, of flexible substrate 31 is inserted. Due to the flexibility of substrate 31 it is possible even with a circumferential groove 102 to insert flexible substrate 31 as it can typically be deformed sufficiently in order to push it in and it then returns to its initial shape. FIG. 5*c* shows an embodiment in which apertures are provided on the margin of flexible substrate 31, one of which is represented in FIG. 5*c*. Pins 103, which fix flexible substrate 31 due to a recess shown in FIG. 5*c*, are snapped into the apertures. The tips of pins 103 are preferably in the shape of truncated cones, as shown in FIG. 5*c*, to make insertion into the apertures of substrate 31 easier. FIG. 5*d* shows a development in which the apertures provided in flexible substrate 31 are used to fix flexible substrate 31 onto fastening area 11 with the help of a screw 104 or another similar fastener.

With regard to fastening area 11, it should be noted that, as shown in FIG. 6, fastening of aerosol generating device 3 in an inhalation therapy unit need not take place around the entire circumference of flexible substrate 31. Fastening may be achieved at only a few, for example 3, points of flexible substrate 31 with the help of an appropriately designed fastening area of the inhalation therapy unit which comprises three partial regions 11*a*, 11*b* and 11*c*. Furthermore, this design offers further advantageous design possibilities in respect of a fastening favourable to oscillation which may be used depending on the application case. For example, fewer/more or larger/smaller fastening areas may be provided. The fastening in sections of flexible substrate 31 to fastening areas 11*a*, 11*b* and 11*c* shown in FIG. 6 corresponds to the variation shown in FIG. 5*b*; nevertheless, it is obvious that other fastening possibilities, for example the variations of FIG. 5*a*, 5*c* or 5*d*, may also be used.

With fastening only in regions around the circumference of flexible substrate 31, as shown in FIG. 7, it is also possible to cut out the regions of the substrate lying between the fastening sections such that tab-like projections 31*a*, 31*b* and 31*c* are formed on the substrate's circumference. It should be noted in respect of FIG. 7 that shown here is the variation of FIG. 5*d* in sectional design; but other fastening possibilities, for example the variations of FIGS. 5*a*, 5*b* and 5*c*, may also be used.

Conductors 34 carried by flexible substrate 31 serve primarily for the supply of electrical signals to actuating device 32. In the Figs. explained previously, the conductors or printed conductors are only shown diagrammatically, basically in order to explain that these conductors are disposed on or in flexible substrate 31. A few advantageous developments of the circuit configuration will be described in the following with reference to FIGS. 8 and 9.

Figure 3A:
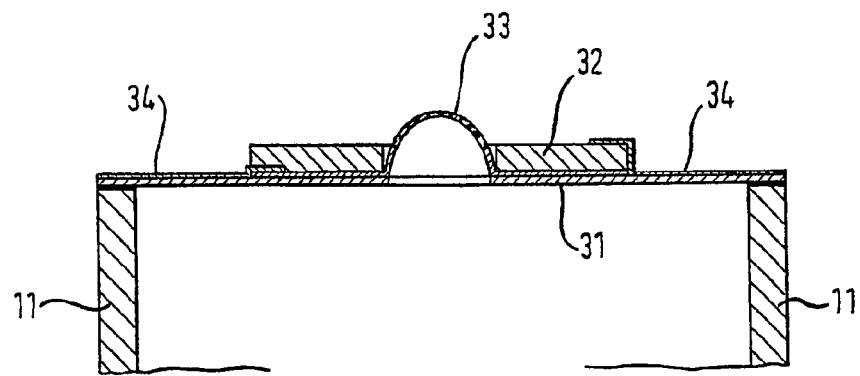
FIGS. 3a, 3b and 3c show various alternative developments of the aerosol generating device according to FIGS. 2a and 2b.
Figure 3B:
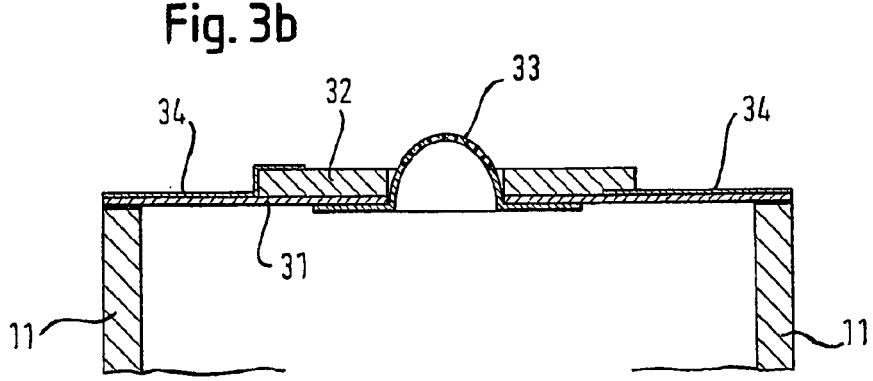
Figure 3C:
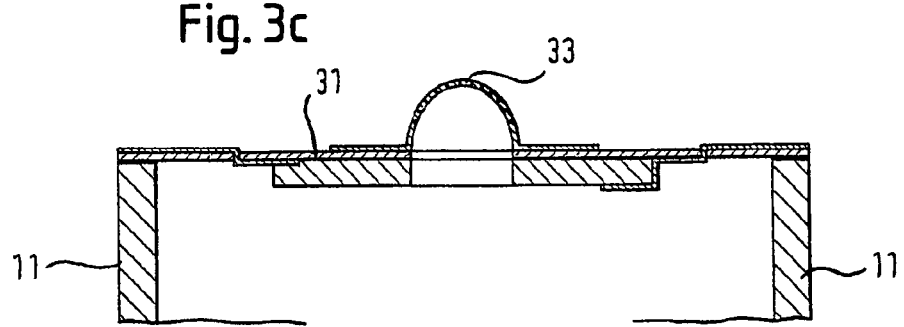
Figure 8:
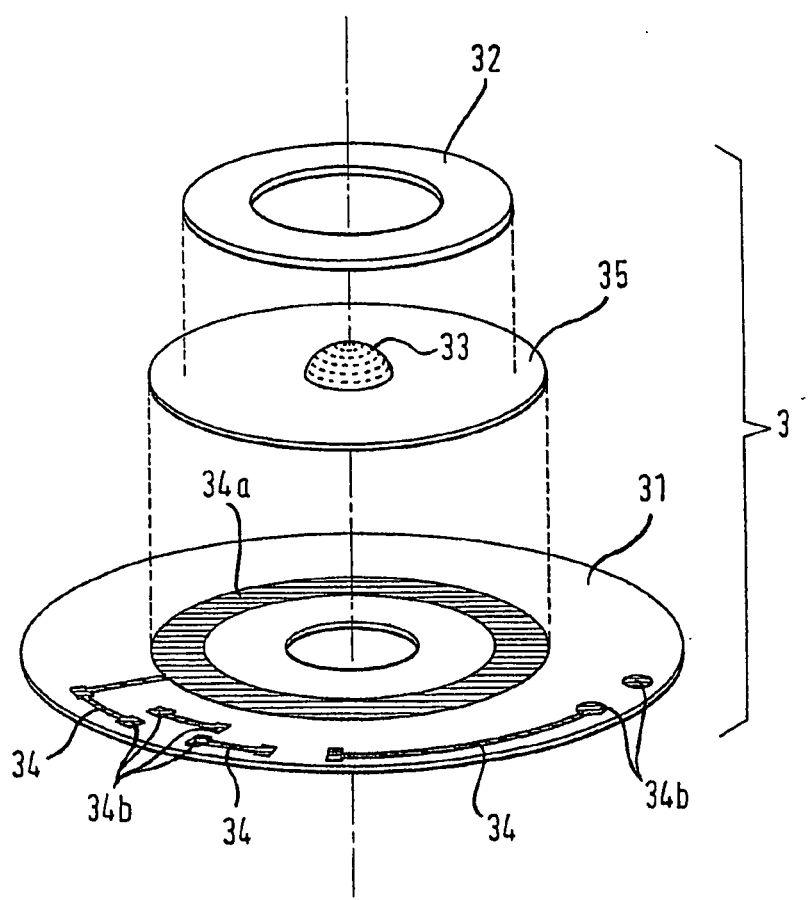
FIG. 8 shows an exploded drawing of a further embodiment of an aerosol generating device according to the invention.
Figure 9:
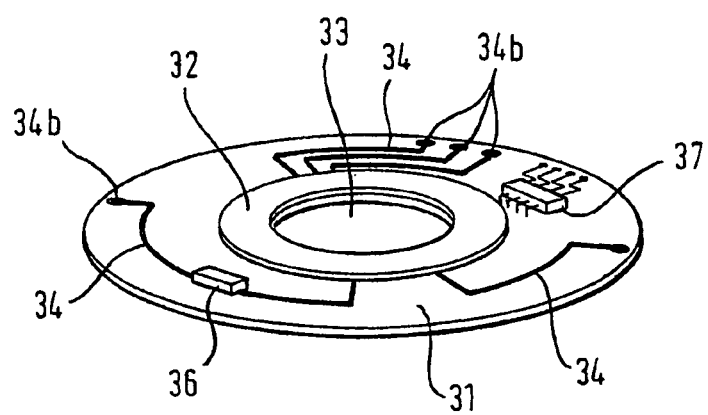
FIG. 9 shows a perspective view of a further embodiment of an aerosol generating device according to the invention.

FIG. 8 shows an exploded drawing of an aerosol generating device 3, whereby with this configuration flexible substrate 31 is provided with a number of conductors 34, 34a and 34b which are applied to flexible substrate 31. A ring-shaped printed conductor 34 is pointed out, which serves advantageously for contacting of actuating device 32, whereby contacting takes place not directly but by way of membrane 33 in the embodiment shown in FIG. 8. Actual realisation of the electrical contacting of actuating device 32 does not pose any problem for the person of average skill in the art even in the alternative configurations referred to above of flexible substrate, actuating device, membrane and optionally further substrate with the result that a description of the various contacting alternatives is superfluous and reference may be made to FIGS. 2 and 3.

Figure 4:
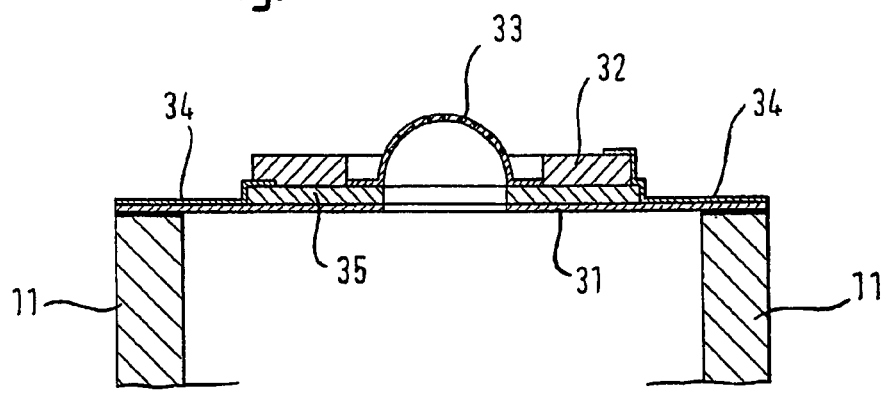
FIG. 4 shows a further embodiment of an aerosol generating device according to the invention.
Figure 5A:
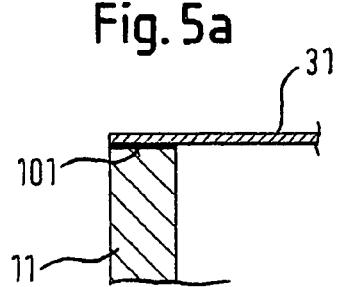
FIGS. 5a, 5b, 5c and 5d show various alternatives for fastening of the aerosol generating device according to the invention.
Figure 5B:
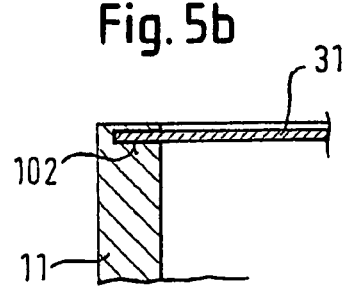
Figure 5C:
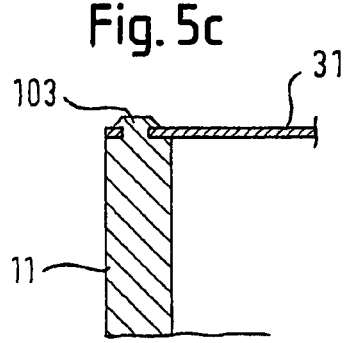
Figure 5D:
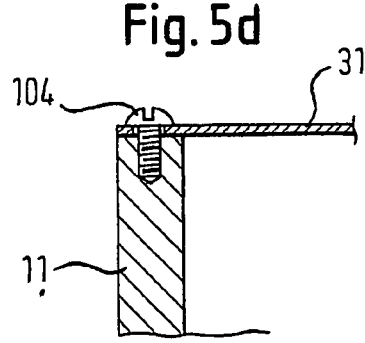
Figure 6:
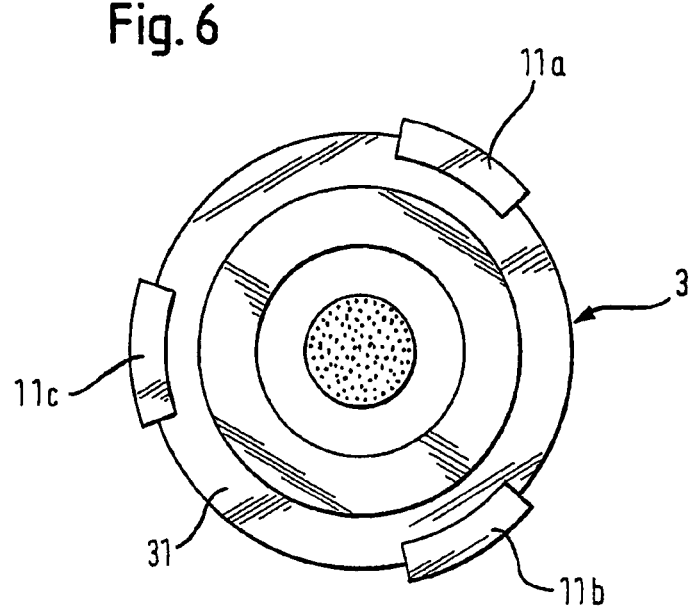
FIG. 6 shows a further alternative for fastening of the aerosol generating device according to the invention.
Figure 7:
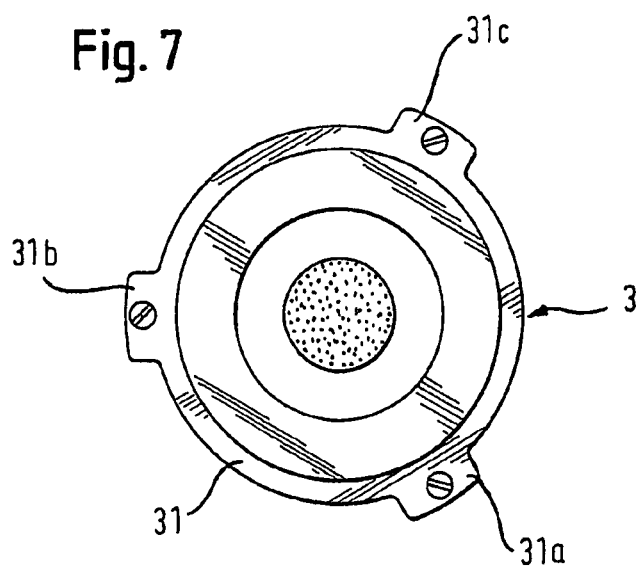
FIG. 7 shows a further alternative for fastening of the aerosol generating device according to the invention.

Alternatively, a specially prepared surface, which is suitable for a bond, may also be provided on this ring-shaped region 34a. In this case, contacting of the appropriate element and bonded fastening do not rule each other out. In the embodiment shown in FIG. 8, membrane 33 is produced in one piece with further substrate 35. Actuating device 32 is disposed according to FIG. 8 on the upper side in the drawing of further substrate 35 combined with the membrane. Alternative developments in respect of this aspect may easily be inferred and emerge, for example, from FIGS. 2, 3 and 4.

Further contact areas 34b are illustrated in FIG. 8 on flexible substrate 31 adjacent to conductors 34 and ring-shaped contact area 34a. Such contact areas serve for the connection of additional electrical components, such as are shown for example in FIG. 9. In the embodiment shown in FIG. 9, a passive component 36 and an active component 37 are provided as an example in order to highlight that using conductors 34 and contact areas 34b creates the possibility of advantageously using the printed circuit board characteristics of flexible substrate 31.

The invention claimed is:

1. Aerosol generating device comprising:
   a membrane for the nebulization of a liquid,
   an actuating device, coupled to the membrane in such a way that, on activation by electrical signals, the actuating device sets the membrane in oscillatory motion, and
   a flexible substrate formed of insulating material,
      which carries a first electrical conductor trace on or in said flexible substrate for supplying electrical signals to a lower side of the actuating device,
      which carries a second electrical conductor trace on or in said flexible substrate for supplying electrical signals to an upper side of the actuating device,
      which is attached to the membrane and the actuating device, and
   which has at least one separated third electrical conductor trace on or in said flexible substrate with a contact area,
   wherein said actuating device is bonded or soldered to said flexible substrate, so that said actuating device, said flexible substrate, and said membrane define an oscillatable structure providing oscillations of said membrane, said actuating device and said flexible substrate, in response to activation of said actuating device, out of a plane which is spanned by said flexible substrate, said actuating device, and said membrane.

2. Aerosol generating device according to claim 1, wherein the membrane is surrounded substantially in a ring shape by the actuating device.

3. Aerosol generating device according to claim 1, wherein the membrane is surrounded substantially in a ring shape by the flexible substrate.

4. Aerosol generating device according to claim 1, wherein the actuating device is joined to the membrane in such a manner that the membrane is excited to flexural oscillations on activation of the actuating device.

5. Aerosol generating device according to claim 1, wherein the actuating device comprises a piezoelectric element.

6. Aerosol generating device according to claim 1, wherein a further substrate is provided for a reciprocal action with the actuating device.

7. Aerosol generating device according to claim 6, wherein the further substrate consists of a metal.

8. Aerosol generating device according to claim 6, wherein the further substrate is formed in one piece with the membrane.

9. Aerosol generating device according to claim 1, wherein the flexible substrate is a printed circuit board, a flexible circuit board or a conductor foil.

10. Aerosol generating device according to claim 9, wherein one or more of the first, second and third electrical conductor traces are applied to the flexible substrate or are integrated in the flexible substrate as printed conductors.

11. Aerosol generating device according to claim 9, wherein contact surfaces are provided on at least one surface of the flexible substrate.

12. Aerosol generating device according to claim 11, wherein further electrical components are disposed on the flexible substrate.

13. Aerosol generating device according to claim 1, wherein the flexible substrate is of multi layer construction.

14. Aerosol generating device according to claim 1, wherein the flexible substrate has a plurality of fastening sections.

15. Aerosol generating device according to claim 14, wherein the plurality of fastening sections is disposed on the circumference of the flexible substrate.

16. Aerosol generating device according to claim 1, wherein the flexible substrate is capable of joining on a circumference of the flexible substrate to a fastening area of an inhalation unit.

17. Aerosol generating device according to claim 1, wherein the flexible substrate is capable of being bonded, inserted, snapped in or clamped in.

18. Inhalation therapy unit having a fastening area for fastening of an aerosol generating device according to claim 1.

19. Aerosol generating device according to claim 1, whereby the thickness of said flexible substrate is like that of said membrane.

20. Aerosol generating device according to claim 1, whereby said first electrical conductor trace on or in said flexible substrate supplies electrical signals to said lower side of the actuating device directly or indirectly via a further substrate.

21. Aerosol generating device according to claim 20, whereby said second electrical conductor trace on or in said flexible substrate supplies electrical signals to said upper side of the actuating device directly or indirectly via said further substrate.

22. Aerosol generating device comprising:
   a membrane for the nebulization of a liquid, an actuating device, coupled to the membrane in such a way that, on activation by electrical signals, the actuating device sets the membrane in oscillatory motion,
a flexible substrate formed of insulating material,
which carries a first electrical conductor trace on or in said flexible substrate for supplying electrical signals to the actuating device, and
a further metallic substrate produced in one piece with said membrane, wherein said further metallic substrate is tuned to said actuating device such that, on activation of said actuating device, flexural oscillations out of a plane spanned by said flexible substrate, said actuating device and said further metallic substrate are set in motion,
wherein said actuating device is bonded or soldered to said flexible substrate, so that said actuating device, said flexible substrate, and said membrane define an oscillatable structure providing oscillations of said membrane, said actuating device and said flexible substrate, in response to activation of said actuating device, out of a plane which is spanned by said flexible substrate, said actuating device, and said membrane.

\* \* \* \* \*